United States Patent [19]
Watanabe

[11] Patent Number: 6,063,427
[45] Date of Patent: May 16, 2000

[54] METHOD FOR PRODUCING A HYPOALLERGENIC WHEAT FLOUR

[75] Inventor: Michiko Watanabe, Tokyo, Japan

[73] Assignee: Japan Science and Technology Corporation, Japan

[21] Appl. No.: 08/774,354

[22] Filed: Dec. 27, 1996

[30] Foreign Application Priority Data

Dec. 28, 1995 [JP] Japan ................................. 7-344069
Dec. 28, 1995 [JP] Japan ................................. 7-344070

[51] Int. Cl.$^7$ ............................. A21D 8/04; A21D 8/00
[52] U.S. Cl. ........................ 426/549; 426/42; 426/391; 530/350; 514/12
[58] Field of Search .................... 426/549, 391, 426/42; 530/350; 514/12

[56] References Cited

U.S. PATENT DOCUMENTS 3,650,764  3/1972  Duquette ..................... 99/90
4,670,268  6/1987  Mahmoud .................... 426/72

OTHER PUBLICATIONS

Watanabe et al. (1995) Biosci. Biotach. Biochem. 59(8): 1596–1597.
Watanabe et al. (1994a) Biosci. Biotech. Biochem. 58(2): 388–390, Feb. 1994.
Watanabe et al. (1994b) Biosci. Biotech. Biochem. 58(11): 2061–2065.
Ikezawa et al. Biological Abstracts vol. 098, lss. 9, Ref. 111531, 1994.
Ishida et al. J. Jpn. Soc. Food Sci. Technol. 36(12): 1003–1008 English Abstract, 1989.
S. Tanabe et al., *Biochemical and Biophysical Research Communications*, 219, 290–293 (1996).
S. Tanabe et al., *Biochemical and Biophysical Research Communications*, 223, 492–495 (1996).
M. Watanabe et al., *Biosci. Biotech. Biochem.*, 59(8), 1596–1597 (1995).
M. Watanabe et al., *Food Sci. Technol. Int.*, 2(1), 10–15 (1996).

*Primary Examiner*—Chris Eisenschenk
*Assistant Examiner*—Mary K. Zeman
*Attorney, Agent, or Firm*—Wenderoth, Lind & Ponack, L.L.P.

[57] ABSTRACT

The present invention provides a method for producing a hypoallergenic wheat flour, which comprises mixing water or aqueous ethanol solution to wheat flour, and then mixing a protease having a high collagenase-like activity and being applicable to food preparation with the mixture. The present invention also provides a hypoallergenic wheat flour produced by the above method, and wheat flour processed food products made from this hypoallergenic wheat flour as a raw material. The present invention makes it possible for a patient suffering from wheat-associated allergy to safely take various food products made from the wheat flour.

5 Claims, 6 Drawing Sheets

(▶ indicates the band of bromelain)

SEQUENCE LISTING (1) GENERAL INFORMATION:

(iii) NUMBER OF SEQUENCES:  5

(2) INFORMATION FOR SEQ ID NO:1:

(i) SEQUENCE CHARACTERISTICS:
      (A) LENGTH:  30
      (B) TYPE:   amino acid
      (C) STRANDEDNESS:
      (D) TOPOLOGY:  linear    (ii) MOLECULE TYPE:  peptide   (iii) HYPOTHETICAL:

(iv) ANTI-SENSE:

(v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION: SEQ ID NO:1:

Ser Gln Gln Gln Gln Pro Pro Phe Ser Gln Gln Gln Pro Pro Phe
 1               5                  10                  15

Ser Gln Gln Gln Gln Pro Pro Phe Ser Gln Gln Gln Pro Pro Phe
                20                  25                  30

(2) INFORMATION FOR SEQ ID NO:2:

(i) SEQUENCE CHARACTERISTICS:
             (A) LENGTH:  5
             (B) TYPE:  amino acid
             (C) STRANDEDNESS:
             (D) TOPOLOGY:  linear (ii) MOLECULE TYPE:  peptide (iii) HYPOTHETICAL:

(iv) ANTI-SENSE:

(v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION: SEQ ID NO:2:

Gln Gln Gln Pro Pro
 1               5

(2) INFORMATION FOR SEQ ID NO:3:

(i) SEQUENCE CHARACTERISTICS:
             (A) LENGTH:  5
             (B) TYPE:  amino acid
             (C) STRANDEDNESS:
             (D) TOPOLOGY:  linear (ii) MOLECULE TYPE:  peptide (iii) HYPOTHETICAL:

(iv) ANTI-SENSE:

(v) FRAGMENT TYPE:

(vi) ORIGINAL SOURCE:

(vii) IMMEDIATE SOURCE:

(viii) POSITION IN GENOME:

(ix) FEATURE:
             (A) NAME/KEY:
             (B) LOCATION:
             (C) IDENTIFICATION METHOD:
             (D) OTHER INFORMATION:  Xaa represents an arbitrary
                 amino acid residue (x) PUBLICATION INFORMATION:

(xi) SEQUENCE DESCRIPTION: SEQ ID NO:3:

```
Gln Xaa Xaa Pro Pro
  1           5

(2) INFORMATION FOR SEQ ID NO:4:

(i) SEQUENCE CHARACTERISTICS:
        (A) LENGTH:  7
        (B) TYPE:   amino acid
        (C) STRANDEDNESS:
        (D) TOPOLOGY:  linear (ii) MOLECULE TYPE:  peptide (iii) HYPOTHETICAL:

(iv) ANTI-SENSE:

(v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION: SEQ ID NO:4:

Ser Gln Gln Gln Pro Pro Phe
  1               5

(2) INFORMATION FOR SEQ ID NO:5:

(i) SEQUENCE CHARACTERISTICS:
        (A) LENGTH:   8
        (B) TYPE:   amino acid
        (C) STRANDEDNESS:
        (D) TOPOLOGY:  linear (ii) MOLECULE TYPE:  peptide (iii) HYPOTHETICAL:

(iv) ANTI-SENSE:

(v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION: SEQ ID NO:5:

Ser Gln Gln Gln Gln Pro Pro Phe
  1               5
```

METHOD FOR PRODUCING A HYPOALLERGENIC WHEAT FLOUR

FIELD OF THE INVENTION

The present invention relates to a method for producing a hypoallergenic wheat flour and a hypoallergenic wheat flour produced by the method. More particularly, the present invention relates to a hypoallergenic wheat flour useful as a food material for cereal-allergy patients and a wheat-flour processed foods available from such a wheat flour.

DESCRIPTION OF THE RELATED ART

The number of patients suffering from food allergy is increasing throughout the world. Cereal-associated allergy is considered to be particularly a serious problem, because cereals such as rice and wheat are consumed as the staple food in most countries.

To solve this problem, the present inventors developed a low-allergen rice in 1990 (J. Food Sci., 55, p. 781, 1990; J. Food Sci., 55, p. 1105, 1990; J. Nutrition, 44, p. 51, 1991; Trends Food Sci., 4, 1993). The developed product was approved in 1993 as the first physiologically functional food for specified health uses by the Japanese Ministry of Health and Welfare, and is now being commercially supplied widely to patients with rice-associated allergy.

On the other hand, although wheat flour is used in quantities as a raw material for bread, noodles and pasta serving as the stable food for many people in the world, achievement of a hypoallergenic wheat floor applicable to food preparation has not as yet been successful to date. In this respect, the present inventors isolated a wheat-antigenic peptide having the amino acid sequence of SEQ ID NO. 1 from a chymotrypsin hydrolysate of gluten which is an antigen for most of wheat-allergy patients (Biosci. Biotech. Biochem., 59, p. 1596–1607, 1995), and found out that the epitope of this peptide is the portion of the amino acid sequence shown in SEQ ID NO. 2, and that the amino acid residues essential for the epitope function are glutamine residue (Gln) first from the N-terminal and the fourth and fifth proline residues (Pro) (Proceedings of anual meeting of Jap. Agr. Chem., 1995). With a view to inactivating epitope of this wheat allergen, the present inventors successfully produced a hypoallergenic wheat flour by treating the flour with collagenase which recognized proline residue, and processed the resultant wheat flour into bread and pasta (Biosci. Biotech. Biochem., 58, p. 388–390, 1994).

However, since this collagenase is an enzyme produced from an anaerobic bacillus, Clostridium, it is not approved as a food additive, and has a definitive drawback in that hypoallergenic wheat flour treated with collagenase is not applicable to food preparation as a raw material.

SUMMARY OF THE INVENTION

The present invention has an object to provide a method for producing a hypoallergenic wheat flour applicable to food preparation and a resultant hypoallergenic wheat flour, as well as wheat flour processed food products produced from this hypoallergenic wheat flour.

The present invention provides a method for producing a hypoallergenic wheat flour, which comprises the steps of mixing water or an aqueous solution of ethanol to wheat flour, and then mixing a protease having a high collagenase-like activity and being applicable to food preparation with the mixture.

In an embodiment of this method, the protease should preferably be an enzyme having a low amylase activity, in addition to a high collagenase-like activity. More specifically, bromelain is the most suitable as the protease used in the method of the present invention because of a high collagenase-like activity and a low amylase activity.

In another embodiment of the foregoing method, furthermore, water in an amount of from 0.05 to 100 times, or more preferably, from 0.1 to 10 times, or an aqueous ethanol solution having a concentration of up to 20% in an amount of from 0.05 to 100 times, or more preferably, from 0.1 to 10 times, should be mixed with the flour to prepare a mixture, and the protease in an amount of from 0.01 to 10 wt. %, or more preferably, from 0.1 to 5 wt. % relative to wheat flour should be mixed with the mixture.

The foregoing method is applicable to any of various types of wheat flour such as hard flour, quasi-hard flour, medium flour and soft flour.

The present invention provides a hypoallergenic wheat flour, of which the epitope of IgE-binding site having the the amino acid sequence of SEQ ID NO. 2 or 3 is inactivated.

The present invention further provides a wheat flour processed food products produced from the hypoallergenic wheat flour as a raw material. These wheat flour processed food products include all products of wheat flour such as bread, noodles, coatings of shao-mais and the like, pasta, pizza dough and cakes.

The present invention more further provides a manufacturing method of a hypoallergenic bread, which comprises the steps of mixing a carbonate and an acid with the hypoallergenic wheat flour thereby generating carbon dioxide from the mixture, and then baking the mixture.

In addition, the present invention provides also a peptide and a peptide derivative having the amino acid sequence of SEQ ID NO. 2 or 3, the derivative having acetylates glutamine residue at the N-terminal. This peptide and peptide derivative serve as a haptene molecule because they have a binding ability with IgE against wheat allergen but not having antigenicity.

DETAILED DESCRIPTION OF THE INVENTION

The epitope of wheat flour, which is the basis of the method for producing a hypoallergenic wheat flour of the present invention was determined as follows.

1. Isolation of Wheat Antigenic Peptide:

Gluten from soft flour (Showa Sangyo Co.; commercial name: Cleopatra) was freeze-dried and then pulverized. After sterilization, the gluten powder was hydrolyzed with the use of chymotripsin. More specifically, α-chymotrypsin (0.5 g, Sigma Chemical Co., Type II, 40–60 units/mg of protein) was dissolved in water (10 ml), and then filtered through a 0.45 μm pore-sized filter. The filtrate was dissolved in autoclaved water (2.5 l) and mixed with 50 g gluten powder. The resultant mixture was pH-adjusted to 7 with 0.1N NaOH, and hydrolyzed at 37° C. for 18 hours. The resulting reaction product was heated at 60° C. for five minutes to inactivate the enzyme, and then, centrifuged (1,000×g for 10 minutes) to obtain a supernatant. This supernatant, after vacuum concentration, was submitted to gel filtration.

Figure 1:
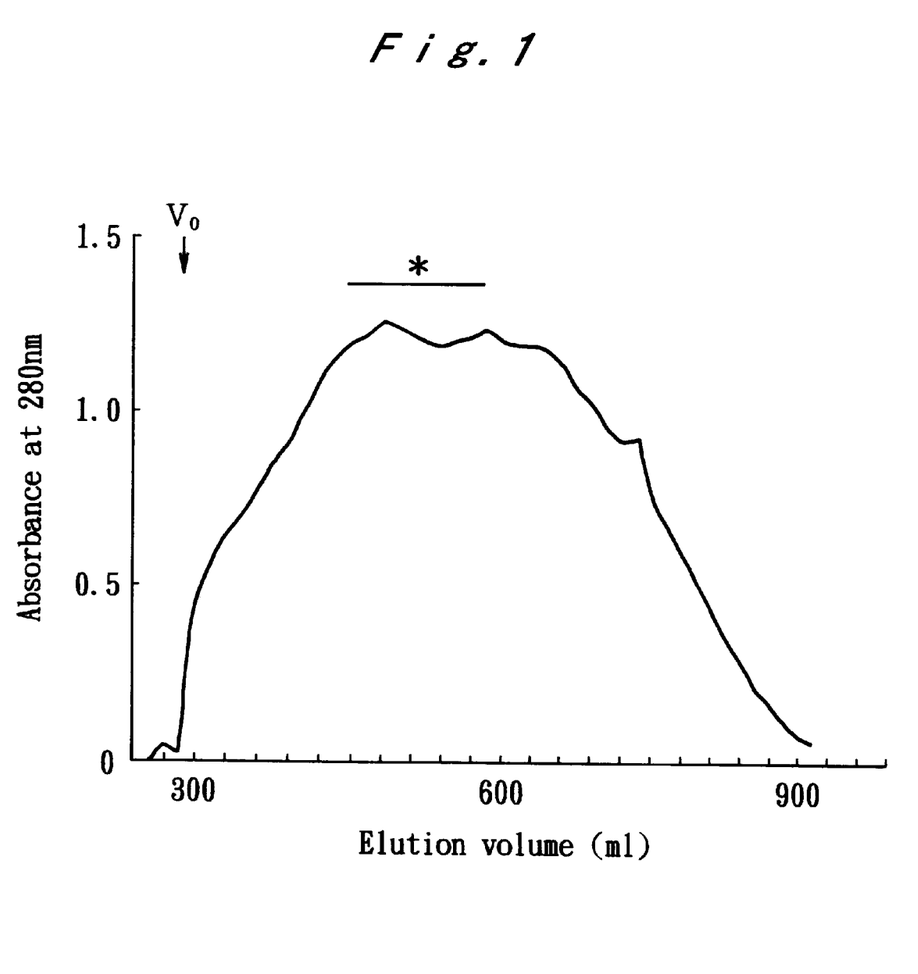
FIG. 1 illustrates a gel filtration pattern of chymotryptic hydrolysate of gluten.

A Sephadex G-50 column (4.9×45 cm, $V_o$=255 ml) was used for the gel filtration, and the chymotriptic hydrolysate was eluted with 10% ethanol. FIG. 1 shows a typical gel filtration pattern of the chymotriptic hydrolysate. The elute in 50-ml portions was collected as one fraction. Each fraction was freeze-dried, and the dried powder (50 mg) was dissolved in 0.1N Tris-HCl (pH: 8.6) containing 4M urea. The solution was then subjected to allergenicity measurement by the IgE-ELISA method, using the serum of a patient with wheat-associated allergy (provided by Urafune Hospital of Yokohama City University School of Medicine) in terms of binding property with the specific IgE antibody in the serum. The fraction indicated with an asterisk in FIG. 1 was found to be allergenic.

Figure 2A:
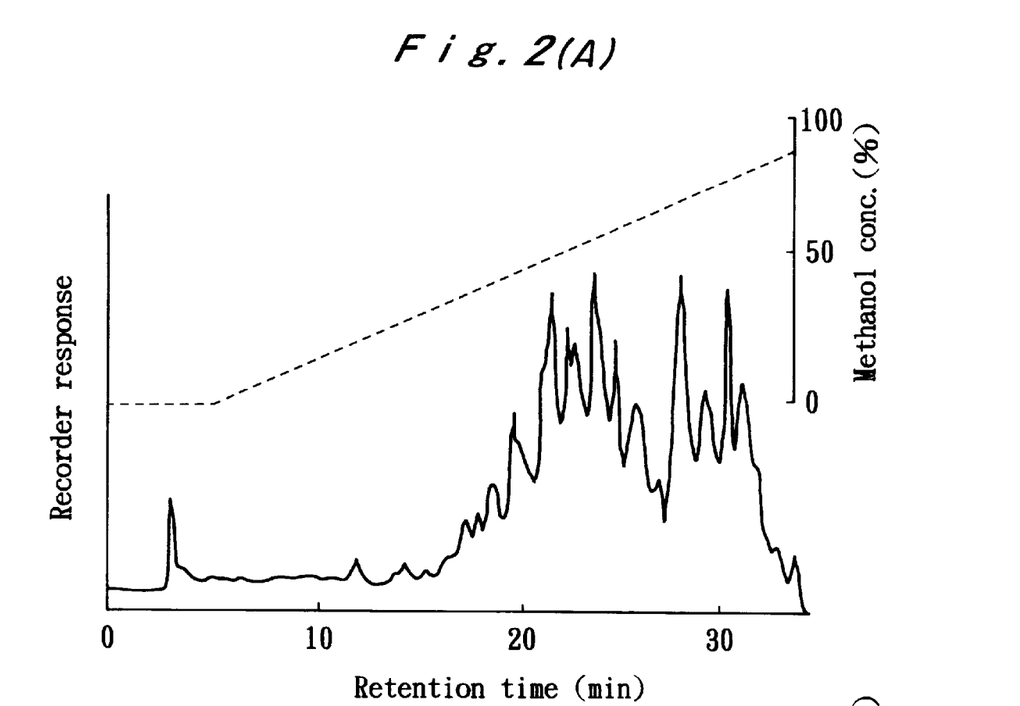
FIG. 2(A) illustrates a chromatogram of chymotryptic hydrolysate of gluten and FIG. 2(B) a chromatogram of an antigenicity peak.
Figure 2B:
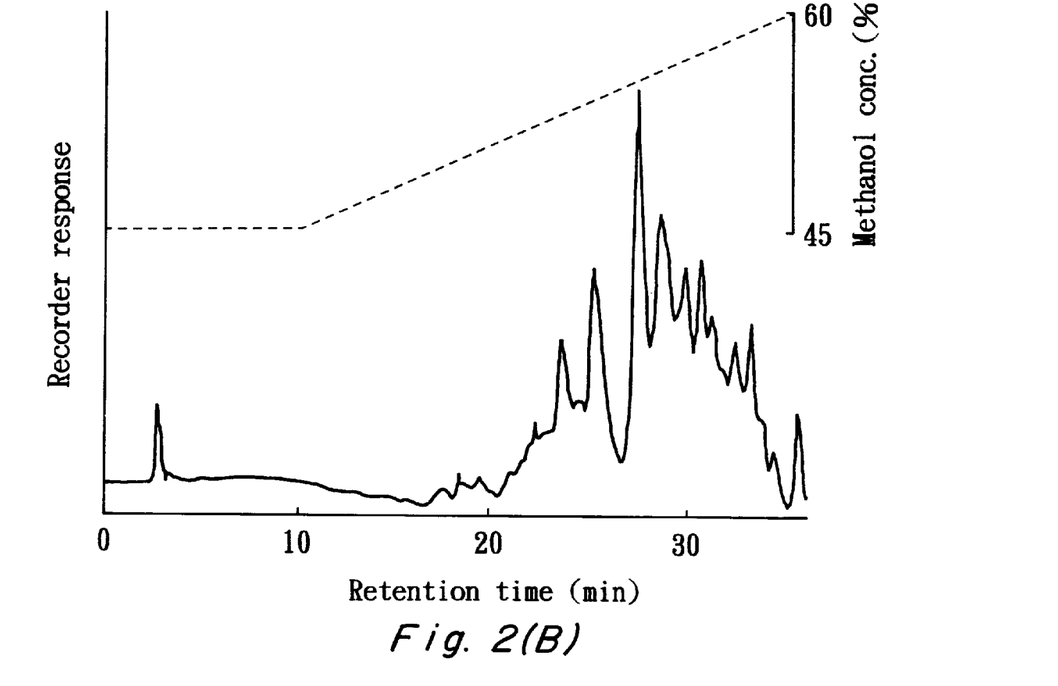

This allergenic fraction was subjected to high performance liquid chromatograph (HPLC) with an ODS column at 22° C. A linear gradient of 0.1% trifluoroacetic acid-methanol (0 to 75% in methanol concentration) was used as the eluting solution, and UV at 210 nm was used for detection. The ELISA data from the peaks in FIG. 2A demonstrates that the numbered peaks were allergenic. Peak 2 (with higher allergenicity) in FIG. 2A was further fractionated by the second HPLC by modifying the solvent system in a gradient manner (45 to 60% with respect to methanol concentration). The asterisked peak (FIG. 2B) obtained by the second HPLC was judged to be allergenic to the highest degree. This peak was chromatographed three times to isolate allergenic peptide.

The amino acid sequence of the allergenic peptide thus obtained was determined by means of an amino acid sequencer (Applied Biosystems Co., 477A). As a result, this peptide was confirmed to have an amino acid sequence of SEQ ID NO. 1. The peptide contains much proline and glutamine resides, and have a unique repeated sequence as shown in SEQ ID NOS. 4 and 5 (hereinafter referred to as "SQQQ (Q)PPF"). A similarity test revealed that the amino acid sequence of this peptide had a similarities of from 70 to 90% with the low-molecular-weight glutenin precursor, and the isolated allergenic peptide was found to have come from the low-molecular-weight glutenin.

The foregoing allergenic peptide can be used for identification of allergen genes in wheat genome by the application of DNA analysis thereof, and therefore greatly contributes to achievement of hypoallergenic what flour based on gene manipulation.

2. Determination of Epitope Site of Allergenic Peptide:

For the purpose of determining the epitope structure of the allergenic peptide obtained in 1. above, it was examined whether or not the motif SQQQ(Q)PPF is involved in binding to specific IgE antibodies in the sera from patients allergic to wheat. More specifically, peptide SQQQ(Q)PPF, (SQQQ(Q)PPF)×2, and (SQQQ(Q)PPF)×4 were synthesized by the application of the known solid phase peptide synthesis (Proc. Natl. Acad. Sci. U.S.A., 81, p. 3,998–4,002, 1984), and the binding property of each peptide with IgE antibody was measured by the ELISA method. The results are as shown in Table 1: irrespective of the presence of repetition, antibody binding ability was almost the same for all cases. There was observed almost no difference in binding ability also for SQQQPPF having a number of glutamine smaller by one.

To examine which amino acid residues in the motif essentially contribute to bind to IgE antibody, it was tried to replace each of the constituent amino acid residues by glycine (G), and the antibody binding ability was measured by ELISA. As a result, as shown in Table 1, replacement of glutamine residue (Q) second from the N-terminal of SQQQ (Q)PPF sequence and two proline residues (P) led to a considerable decrease in the antibody binding ability. It was furthermore confirmed that a shorter peptide QQQPP (SEQ ID NO. 2) had as well a high antibody binding ability. In addition, because the second and the third glutamine residues from the N-terminal of this QQQPP sequence are replaceable with other arbitrary amino acid residues, it was confirmed that the epitope of wheat-antigenic peptide was the QQQPP sequence portion, and amino acid residues essential for antibody binding ability thereof were the first glutamine residue from the N-terminal and the fourth and the fifth proline residues therefrom. Another confirmation is the fact that an acetylated amino group at the N-terminal leads to a higher antibody binding ability than a free amino group.

TABLE 1

| Peptide | Relative ELISA value |
| --- | --- |
| Ac · S · Q · Q · Q · Q · P · P · F · | 1.0* |
| S · Q · Q · Q · P · P · F · | |
| S · Q · Q · Q · Q · P · P · F · | |
| S · Q · Q · Q · P · P · F. | |
| Ac · S · Q · Q · Q · Q · P · P · F · | 1.1 |
| S · Q · Q · Q · P · P · F | |
| Ac · S · Q · Q · Q · Q · P · P · F · | 1.1 |
| Ac · S · Q · Q · Q · P · P · F | 1.0 |
| Ac · G · Q · Q · Q · P · P · F | 1.1 |
| Ac · S · G · Q · Q · P · P · F | nd** |
| Ac · S · Q · G · Q · P · P · F | 0.8 |
| Ac · S · Q · Q · G · P · P · F | 1.0 |
| Ac · S · Q · Q · Q · G · P · F | nd |
| Ac · S · Q · Q · Q · P · G · F | nd |
| Ac · S · Q · Q · Q · P · P · G | 0.9 |
| Ac · Q · Q · Q · P · P | 0.9 |
| Ac · G · Q · Q · P · P | nd |
| Ac · Q · G · Q · P · P | 0.7 |
| Ac · Q · Q · G · P · P | 1.0 |
| Ac · Q · Q · Q · G · P | nd |
| Ac · Q · Q · Q · P · G | nd |
| Q · Q · Q · P · P | 0.6 |

*Standard.
**Means the value of lower than the limit of detection.

3. Confirmation of Antigenicity of Peptide Derivative:

A peptide derivative (Ac-QQQPP) was prepared by acetylating the N-terminal amino acid residue (glutamine residue) of the synthetic peptide QQQPP, and with the use thereof, an inhibition ELISA (J. Immunol., 151, p. 5354–5363, 1993) was carried out. Gluten extracted with 4M urea as the antigen, and Ac-QQQPP-treated serum of a wheat-allergic patient was used as the antibody.

Figure 3:
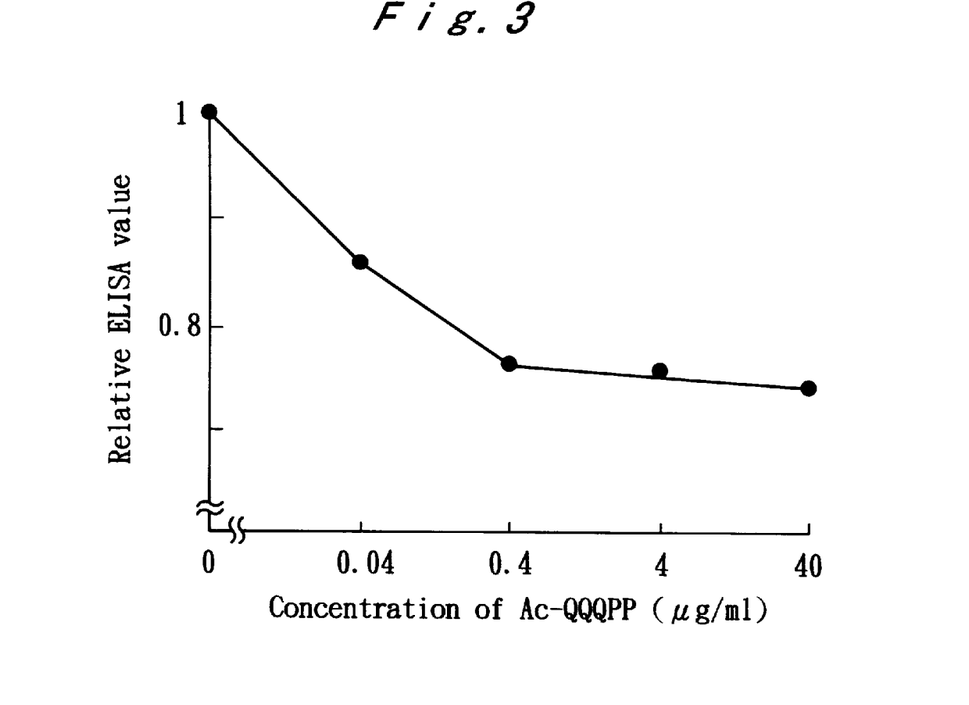
FIG. 3 illustrates concentration-dependent inhibition values of a peptide derivative.

The results are shown in FIG. 3: Ac-QQQPP very well bound to wheat-specific IgE in the serum of the patient.

Then, to examine the correlation between the antibody binding ability and the releasing ability for inflammation mediator such as histamine of this Ac-QQQPP, the amount of histamine released from the basophils was measured in the presence of Ac-QQQPP in accordance with the method proposed by Mita et al (Prostagrandins, 31, p. 869–886, 1980).

Figure 4:
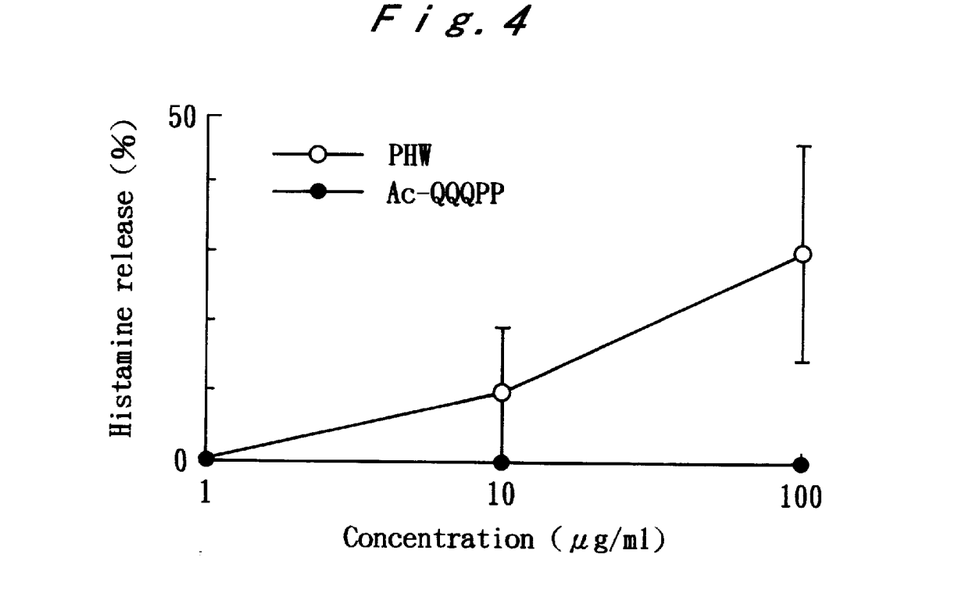
FIG. 4 illustrates changes in the amount of histamine released by the peptide derivative.

As is clear from the results shown in FIG. 4, while pancreatic hydrolysate of wheat flour used as a control caused a concentration-dependent increase in the amount of released histamine, Ac-QQQPP caused no release of histamine in any of the cases examined.

In conclusion, the acetylated derivative of QQQPP derived from the wheat antigenic peptide has a specific binding ability regarding antibody of a wheat-allergic patient, whereas this derivative itself was confirmed to serve as a hapten not causing an antigen reaction such as inflammation. This peptide derivative therefore provides a new possibility in prevention or therapy of wheat-sensitive allergy.

It should be noted in this regard that the peptide having the QQQPP seqeunce has also no antigenicity-expressing ability but has an IgE antibody-binding ability. This may be because the peptide could bind to each of IgE molecule. It is known that an antigenic protein expresses its antigenicity by binding onto at least two molecules of IgE. Therefore, the peptide as well as the peptide derivative which have bound to each IgE does not express antigenicity, and further can prevent binding of antigenic protein onto the IgE molecules.

Now, the method of producing a hypoallergenic wheat flour of the present invention will be described below. The method essentially comprises the steps of mixing water or an aqueous ethanol solution to wheat flour, then mixing a protease having a high collagenase-like activity and being applicable to food preparation with the mixture, and drying the mixture.

When mixing water to raw material wheat flour, the amount of added water should be within a range of from 0.05 to 100 times, or preferably, from 0.1 to 10 times relative to the wheat flour. When mixing the aqueous ethanol solution, the amount of added aqueous ethanol solution having a concentration of up to 20% should be within a range of from 0.05 to 100 times, or preferably, from 0.1 to 10 times relative to the wheat flour. The amount of protease to be mixed with the mixture of flour and water or ethanol solution should be within a range of from 0.01 to 10 wt. %, or preferably, from 0.1 to 5 wt. % of the wheat flour.

The protease to be used should preferably be one having a low amylase activity in addition to the above condition. Effectiveness of the protease having a high collagenase-like activity is evident from the findings that recognition of proline residue of wheat flour epitope (peptide of SEQ ID NO. 2) by collagenase permits achievement of a hypoallergenic wheat flour. Effectiveness of the protease having a low amylase activity is attributable to the fact that decomposition of wheat starch by amylase results in a decreased volume of wheat flour and a serious damage to processability because of the addition of sweetness, and further, that, since amylase inhibitor in wheat protein acts as an antigen for a wheat-sensitive allergic patient, it is impossible to inhibit decomposition of wheat starch by adding amylase inhibitor.

The following Test 1 proved that bromelain is the most suitable protease satisfying these conditions.

TEST 1

This test was carried out to select a protease which has a high collagenase-like activity and a low amylase activity, and is applicable to food preparation.

(1) Samples

Wheat flour: Soft wheat flour (Showa Sangyo Co., commercial name: Cleopatra) was used.

Enzymes: Protease A, protease B, protease S, protease N, proleather, papain W-40 (made by Amano Seiyaku Co.), bromelain (reagent: bromelain; Wako Seiyaku Co.), and maxrase (Riken Pharma Co.) were employed.

(2) Procedure

Collagenase-like activity: The collagenase-like activity was measured in compliance with the method proposed by Van Wart (Anal. Biochem., 113, p. 356–365, 1981) using FALGPA as a substrate. FALGPA decomposing reaction was caused at 25° C. under conditions including a substrate concentration of 0.05 mM, a solvent of 0.4 M NaCl-10 mM $CaCl_2$-50 mM tris-hydrochloric acid buffer solution (pH: 7.5) and an enzyme concentration of 5 mg/ml, to measure the decrease in absorbance of 324 nm for a few minutes. The enzymatic activity was expressed in [units/mg enzyme], where 1 unit represents an activity for hydrolyzing 1 $\mu$mol FALGPA within a minute, and is equal to $\Delta A=0.0025$/minute.

Amylase activity: The substrate, a 1% potato starch, was subjected to an enzymatic reaction at 37° C. for 30 minutes, and the quantity of reducing group was determined by the method proposed by Luchsinger and Cornesky (Anal. Biochem., 4, p. 346–347, 1962). The enzymatic activity was expressed in [$\mu$mol glucose equivalent/minute/mg enzyme].

(3) Results:

The results of this test are shown in Table 2. As is clear from Table 2, the collagenase activities of tested protease samples were higher in the order of bromelain>protease B>protease A=papain. Measurement of the amylase activities of the four protease preparation clarified, as shown in Table 2, that the amylase activity is higher in protease A and B, and lower in bromelain and papain with a value about a tenth that of the former.

TABLE 2

| Enzyme | Collagenase-like activity (a) | Amylase activity (b) |
|---|---|---|
| bromelain | 1.52 | 0.072 |
| protease B | 0.78 | 0.703 |
| papain | 0.21 | 0.040 |
| protease A | 0.20 | 0.759 |
| protease N | N.D.(c) | —(d) |
| protease S | N.D. | — |
| proleather | N.D. | — |
| maxrase | N.D. | — |

Note:
a: [units/mg];
b: [$\mu$mol glucose equivalent/min/mg];
c: not detected (<0.008);
d: not measured From the test results as described above, therefore, it was concluded that bromelain was the most desirable as the protease used in the method for producing a hypoallergenic wheat flour of the present invention.

Figure 5:
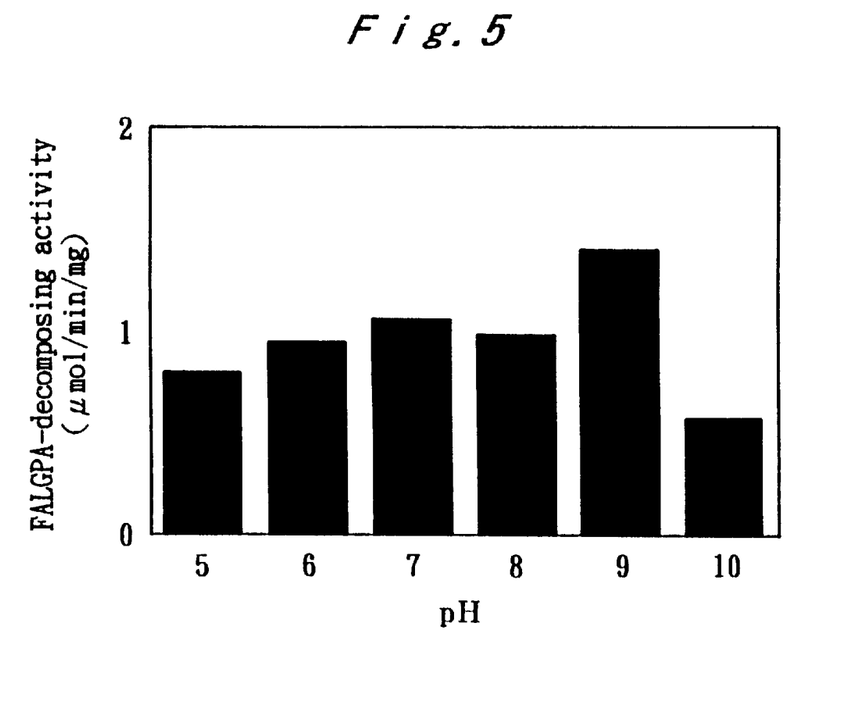
FIG. 5 is a histogram illustrating the pH-dependency of the collagenase-like activity of bromelain.

The collagenase-like activity of bromelain is, as shown in FIG. 5, the highest at a pH of 9. Reaction of bromelain under conditions including a pH of 9 can therefore efficiently reduce antigenicity of wheat flour. With these conditions including a pH of 9, however, flavonoid contained in the wheat flour discolors into yellow because of the alkalinity thereof, and the final product may suffer from discoloration. Although the first of the requirements to be satisfied by a hypoallergenic wheat flour is the absence of antigenicity, it is also required to be well comparable with ordinary wheat flour in terms of quality including color tone. In the method of the present invention, therefore, wheat flour should be reacted under neutral conditions when using bromelain.

As being clear from Test 1, the hypoallergenic wheat flour of this invention can produced by using a protease having high collagenase-like activity, preferably having high collagenase-like and a low amylase activity, and more preferably by using bromelain under neutral conditions. The hypoallergenic wheat flour thus obtained can be used for manufacturing a wheat flour process food, particularly a hypoallergenic bread. The method for manufacturing the bread of this invention consisting essentially of mixing a carbonate and an acid with the hypoallergenic wheat flour as described above, and baking the mixture. Any carbonate and acid applicable to food reparation, such as sodium hydrogen carbonate and citric acid, can be used. By using the carbonate and acid, it is possible to generate carbon dioxide from the mixture of flour at baking without use of baker's yeast.

The present invention will now be described further in detail by means of Examples and Tests. It is needless to mention that the present invention is not limited by the following.

EXAMPLE 1

First, one liter of 10% ethanol was added to, and mixed with, soft wheat flour (1 kg), then 10 g bromelain were added and mixed to the resultant mixture, and after preserving at 37° C. for eight hours, the mixture was freeze dried to prepare a hypoallergenic wheat flour.

EXAMPLE 2

Water in an amount of 1 l was added to, and mixed with, soft wheat flour (1 kg), then 10 g bromelain were added to the resultant mixture, and after preserving at 37° C. for eight hours, the mixture was freeze-dried to prepare a hypoallergenic wheat flour.

EXAMPLE 3

Water in an amount of 0.6 l was added to, and mixed with, soft wheat flour (1 kg), then 10 g bromelain were added to the resultant mixture, and after preserving at 37° C. for one, two, four or eight hours, the mixture was freeze-dried to prepare a hypoallergenic wheat flour.

TEST 2

The antigenicity of the hypoallergenic wheat flour samples prepared in Examples 1, 2 and 3 was tested by the ELISA method as follows.
(1) Procedure The hypoallergenic wheat flour was extracted by means of a 4 M urea-containing tris-hydrochloric acid (UTH) buffer solution (pH: 8.6), and then centrifuged (1,300×g; five minutes). The resultant supernatant was diluted by means of the UTH buffer solution so as to give a peptide concentration of from about 100 to 250 µg/ml. For 100 µl diluted supernatant, the antigenicity was measured by the IgE-ELISA method using, as an indicator, the binding ability with the specific IgE antibody in serum of a wheat-sensitive allergic patient (provided by Urafune Hospital of Yokohama City University School of Medicine).
(2) Results The results are shown in Table 3. As is clear from the results shown in Table 3, the wheat flour samples obtained by adding 10% ethanol or water in the same amount and reacting 1 wt. % bromelain at 37° C. for eight hours (Examples 1 and 2) showed an antigenicity reduced to below the detection limit.

In the wheat flour samples obtained by adding water in an amount 0.6 times to the flour, and reacting 1 wt. % bromolain at 37° C., the antigenicity was decreased to below the detection limit for the eight-hour reaction product, although the antigenicity remains for a reaction time of from one to four hours.

TABLE 3

| Wheat | Manufacturing condition | | | Antigenicity |
|---|---|---|---|---|
| Flour | Solvent | Solvent/Flour | Time (hr) | (ELISA valye) |
| Control | — | — | — | 1 |
| Example 1 | 10% ethanol | 1/1 | 8 | N.D. |
| Example 2 | water | 1/1 | 8 | N.D. |
| Example 3 | water | 0.6/1 | 1 | <0.1 |
| | | 0.6/1 | 2 | <0.1 |
| | | 0.6/1 | 4 | <0.1 |
| | | 0.6/1 | 8 | <N.D. |

TEST 3

The following test was carried out for the hypoallergenic wheat flour sample prepared through reaction of bromolain for eight hours in Example 3.
(1) Procedure SDS-PAGE: A 200 g of hypoallergenic wheat flour and non-treated wheat flour was extracted by means of 1 ml UTH buffer solution and centrifuged (1,300×g; five minutes). Seprasol II (Daiichi Kagaku Co.) in an equal amount was added to the resultant supernatant, and after boiling for 15 minutes, electrophoresis was carried out by means of polyacrylamide gel having a concentration gradient of from 10 to 20% (Daiichi Kagaku Co.) in accordance with the method proposed by Laemmli (Nature, 227, p. 680–685, 1970). Rabbit muscle phosphorylase b (MW, 97 kDa), bovine serum albumin (MW, 67 kDa), opalbumin (MW, 43 kDa), bovine carbonate dehydratase (MW, 31 kDa), soybean trypsin inhibitor (MW, 22 kDa), and chicken albumen lysozyme (MW, 14 kDa) were used as molecular weight markers. After electrophoresis, bands were stained by means of Coomassie Brilliant Blue (R-250; Sigma Co.).

Resistgraphy: Water in an amount of 74 ml was added to, and mixed with, freeze-dried hypoallergenic wheat flour in an amount of 86 g as converted into dry state, and stirred at 30° C. and 63 rpm for 20 minutes with the use of a resistgraph (Brabender Instrument Co.). The same steps were followed also for a mixture of non-treated wheat flour (100 g) and water (60 ml).

Figure 6A:
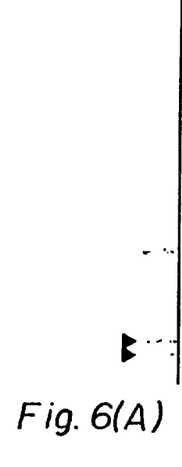
FIG. 6(A) illustrates results of SDS-PAGE of a hypoallergenic wheat flour treated with bromelain and FIG. 6(B) illustrates the same with a non-treated wheat flour.
Figure 6B:
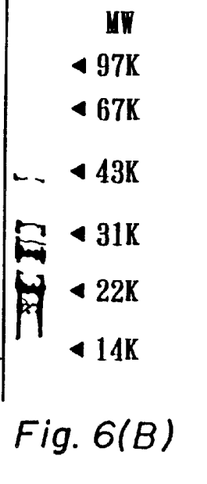

Farmography: Raw baker's yeast (Oriental Kobo Kogyo Co.) was suspended in water in a concentration of 2 g/ml. This yeast suspension (0.345 ml) was mixed with hypoallergenic wheat flour batter (50 g) prepared by the resistgraphy or a wheat flour dough (50 g), and the amount of generated carbon dioxide and the amount retained by the dough were measured at 24° C. for 90 minutes by the use of a farmograph (AR-1000, Art Co.).
(2) Results An SDS-PAGE applied to a 4 M urea extract of the hyperallergenic wheat flour resulted, as shown in FIG. 6, in achievement of hypoallergenicity of most of the hyperallergenic wheat flour samples as compared with a non-treated wheat flour sample so that most thereof came off the gel. Components near 20 kDa to 30 kDa, remaining even after the completion of the reaction, are not considered to have an antigenicity.

Figure 7A:
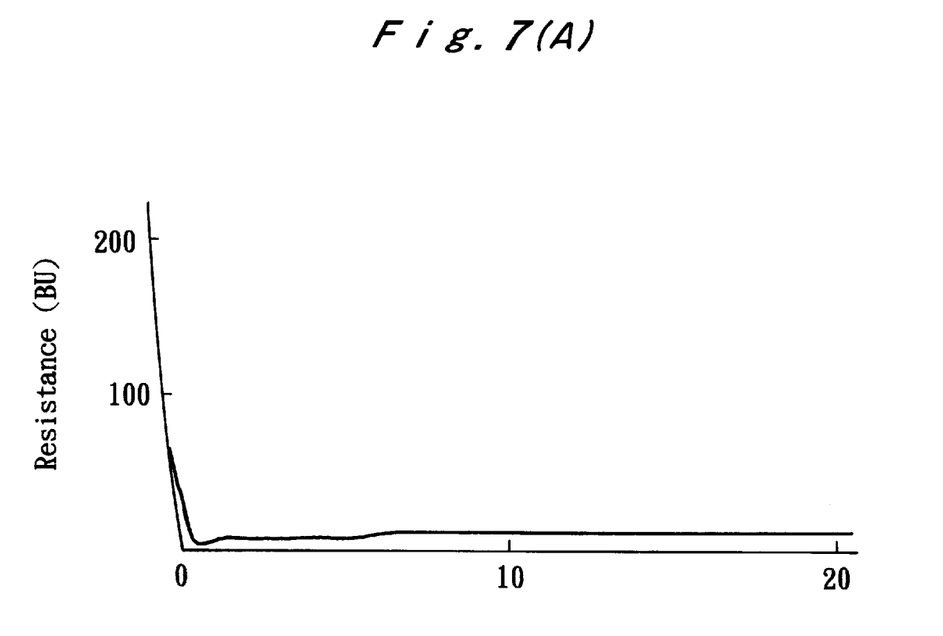
FIG. 7(A) is a resistgram of a hypoallergenic wheat flour treated with bromelain and FIG. 7(B) is a resistgram of a non-treated wheat flour.
Figure 7B:
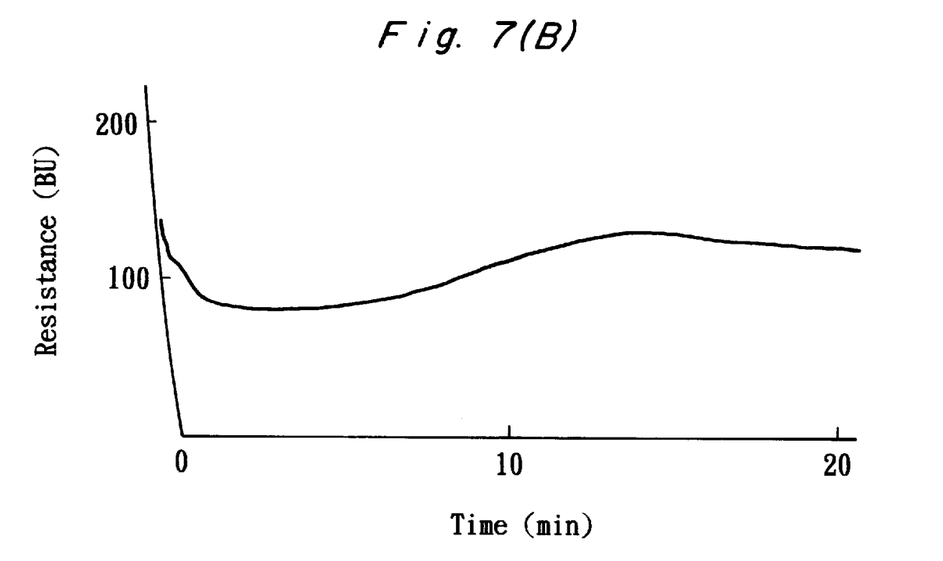
Figure 8:
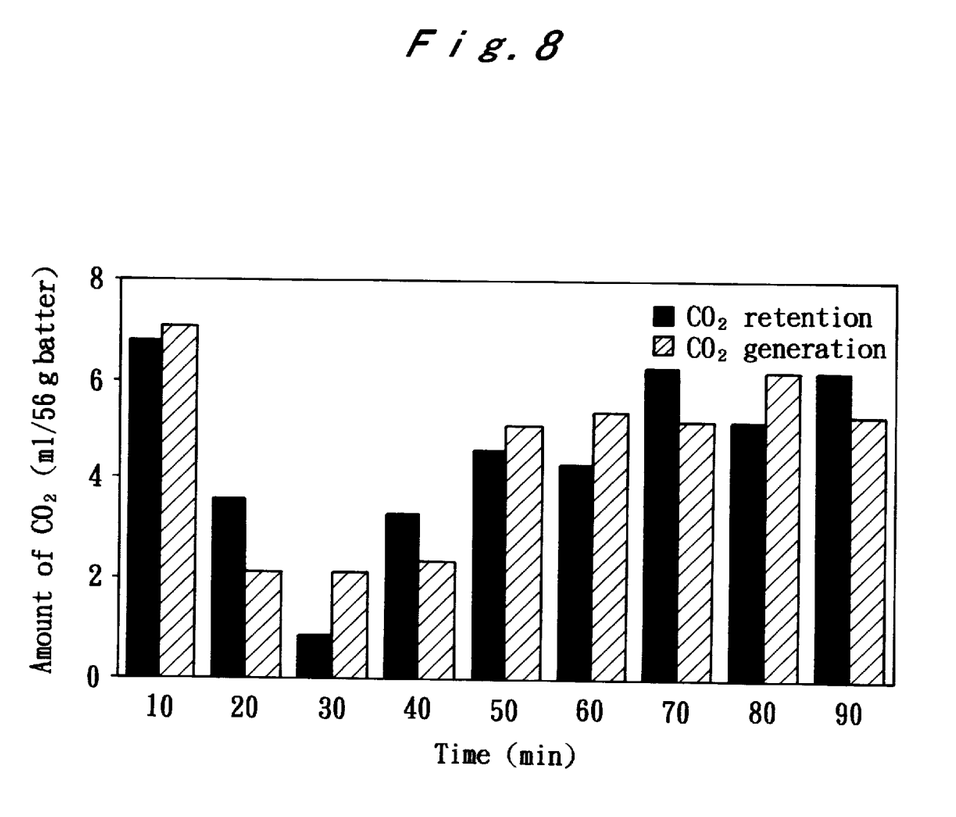
FIG. 8 is a farmogram of the hypoallergenic wheat flour treated with bromelain.

As shown in FIG. 7, the resistgram (A) of the hypoallergenic wheat flour is more flat than that of the non-treated wheat flour, which suggests that no gluten has been formed. As shown in the farmograph of FIG. 8, however, the hypoallergenic wheat flour has a carbon dioxide holding ability, and the possibility was confirmed to manufacture bread and other wheat flour processed food products with the use thereof.

EXAMPLE 4

Water in an amount of 0.6 l was mixed with a soft wheat flour (1 kg), and then 10 g bromolain was added to the mixture and preserved at 37° C. for eight hours. To the bromolain product, 10 g common salt, 10 g glucose, 13 g citric acid, and 10 mg sorbitan monostearate (commercial name: Emasol S-10F, Kao Co.) were added, and the mixture was stirred while further adding 20 g sodium hydrogen carbonate. The mixture in a batch of 30 g each was quickly poured into a 100 ml container or a muffin cup and baked in an oven at 180° C. for 20 minutes to make bread.

Another piece of bread was baked from the hyperallergenic wheat flour through a collagenase treatment (Biosci. Biotech. Biochem., 58, p. 388–390, 1994). Baker's yeast was not used in the pieces of bread made by the foregoing method. Because of the similarity in amino acid sequence between baker's yeast and wheat allergen, a wheat-sensitive allergic patient often presents allergic reaction also to baker's yeast.

Bread was therefore baked by generating carbon dioxide from sodium hydrogen carbonate and citric acid in place of baker's yeast.

TEST 4

This test was examine the properties of the bread baked in Example 4.

(1) Procedure

Specific volume: The loaf volume was measured by the rapeseed replacement method (American Association of Cereal Chemists. in "Approved Methods of the AACC", 8th ed., The Association, St. Paul. Method 10-10B, 1983). The specific volume was expressed in loaf volume (ml)/loaf weight (g).

Color tone evaluation: Color parameters (L, a and b-values) of the upper portion of bread were measured with a color difference meter (SC-2-XCH, Gas Testers Co.).

(2) Results

The test results are shown in Table 4. As is clear from Table 4, the bread from the hypoallergenic wheat flour treated with bromelain has properties similar to those of the bread made from the hypoallergenic wheat flour treated with collagenase in terms of both specific volume and color tone. It has a specific volume similar to that of the commercially available English muffin.

Furthermore, the exterior view and the cross-section of the prepared bread were observed. A fine and smooth bread inner layers were obtained by the addition of sorbitan monostearate. Addition of glucose caused Strecker degradation and Maillard reaction, and the products thereof brought about very good color and fragrance of bread.

TABLE 4

| | Wheat Flour | |
|---|---|---|
| Measurements | Bromelain-treated | Collagenase-treated |
| Specific volume(*) | 3.2 | 3.5 |
| Color parameters: | | |
| L-value | 43.3 | 63.1 |
| a-value | 10.1 | 5.7 |
| b-value | 13.4 | 21.9 |

Note: *: CV-value of the measurement was up to 10%. A commercially available English maffin had a specific volune of 3.0.

What is claimed is:

1. A method for producing a hypoallergenic wheat flour, comprising the steps of mixing water or an aqueous ethanol solution with wheat flour to form a mixture, and then mixing bromelain with the mixture under neutral conditions.

2. The method according to any one of claim 1, wherein the water is added in an amount within a range of from 0.05 to 100 times the amount of the wheat flour.

3. The method according to any one of claim 1, wherein the aqueous ethanol solution having an ethanol concentration of up to 20% is added in an amount within a range of from 0.05 to 100 times the amount of the wheat flour.

4. The method according to claim 1, wherein the bromelain in an amount within a range of from 0.01 to 10 wt. % of the wheat flour is mixed with the mixture.

5. The method according to claim 1, wherein aqueous ethanol is mixed with said wheat flour.

* * * * *